(12) United States Patent
Rowe (10) Patent No.: US 9,095,434 B2
(45) Date of Patent: Aug. 4, 2015

(54) METHOD AND APPARATUS FOR REPLACING A PROSTHETIC VALVE

(75) Inventor: Stanton J. Rowe, Newport Beach, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 0 days.

(21) Appl. No.: 12/986,780

(22) Filed: Jan. 7, 2011

(65) Prior Publication Data

US 2011/0166636 A1    Jul. 7, 2011

Related U.S. Application Data

(63) Continuation of application No. 11/679,750, filed on Feb. 27, 2007, now abandoned.

(51) Int. Cl.
*A61F 2/24* (2006.01)

(52) U.S. Cl.
CPC .............. *A61F 2/2427* (2013.01); *A61F 2/2418* (2013.01); *A61F 2/2433* (2013.01); *A61F 2/243* (2013.01); *A61F 2/2436* (2013.01); *A61F 2220/0008* (2013.01); *A61F 2220/0016* (2013.01); *A61F 2220/0075* (2013.01); *A61F 2230/0054* (2013.01); *A61F 2230/0078* (2013.01); *A61F 2250/006* (2013.01)

(58) Field of Classification Search
CPC ... A61F 2/2418; A61F 2/2409; A61F 2/2427; A61F 2/2433; A61F 2/243
USPC .................... 623/2.11, 2.14, 2.17, 2.18, 1.24; 128/898
See application file for complete search history.

(56) References Cited

U.S. PATENT DOCUMENTS

| 6,425,916 | B1 * | 7/2002 | Garrison et al. ............. 623/2.11 |
| 6,908,481 | B2 | 6/2005 | Cribier |
| 7,708,775 | B2 | 5/2010 | Rowe et al. |
| 7,717,955 | B2 | 5/2010 | Lane et al. |

(Continued)

FOREIGN PATENT DOCUMENTS

| FR | 2874812 | 3/2006 |
| WO | 0047139 | 8/2000 |

(Continued)

OTHER PUBLICATIONS

PCT International Search Report for Application No. PCT/US2008/055160, dated Jul. 16, 2008.

*Primary Examiner* — Gregory Anderson
*Assistant Examiner* — Christopher L Templeton
(74) *Attorney, Agent, or Firm* — Klarquist Sparkman, LLP; David L. Hauser (57) ABSTRACT

In one aspect, the present disclosure concerns a percutaneously delivered adapter stent that is deployed within a previously implanted prosthetic valve and serves as an anchor or platform for implanting a percutaneously delivered replacement valve within the previously implanted valve. The adapter stent can be delivered to the implantation site via the patient's vasculature and positioned within the previously implanted valve. The stent can then be deployed to cause the stent to expand and become anchored to the inner surface of the previously implanted valve. Subsequently, the replacement valve can be positioned within the adapter stent and deployed to cause the replacement valve to expand and become anchored to the adapter stent. The adapter stent and the replacement valve can be mounted on the same catheter for delivery to the implantation site.

15 Claims, 8 Drawing Sheets

(56) References Cited

U.S. PATENT DOCUMENTS

| | | | |
|---|---|---|---|
| 2003/0040792 A1* | 2/2003 | Gabbay | 623/2.11 |
| 2005/0137689 A1* | 6/2005 | Salahieh et al. | 623/2.11 |
| 2005/0240200 A1* | 10/2005 | Bergheim | 606/108 |
| 2005/0251251 A1* | 11/2005 | Cribier | 623/2.11 |
| 2006/0074484 A1* | 4/2006 | Huber | 623/2.11 |
| 2006/0142848 A1* | 6/2006 | Gabbay | 623/1.26 |
| 2006/0247570 A1* | 11/2006 | Pokorney | 604/9 |
| 2006/0287717 A1* | 12/2006 | Rowe et al. | 623/2.11 |
| 2007/0198097 A1* | 8/2007 | Zegdi | 623/23.68 |
| 2007/0244546 A1* | 10/2007 | Francis | 623/1.26 |
| 2008/0161910 A1* | 7/2008 | Revuelta et al. | 623/2.12 |
| 2009/0157174 A1* | 6/2009 | Yoganathan et al. | 623/2.11 |

FOREIGN PATENT DOCUMENTS

| | | | | |
|---|---|---|---|---|
| WO | WO 2005070343 | * | 8/2005 | A61F 2/26 |
| WO | 2007071436 | | 6/2007 | |
| WO | 2008029296 | | 3/2008 | |

* cited by examiner

METHOD AND APPARATUS FOR REPLACING A PROSTHETIC VALVE

CROSS-REFERENCE TO RELATED APPLICATIONS

This application is a continuation of U.S. patent application Ser. No. 11/679,750, filed Feb. 27, 2007 now abandoned.

FIELD

The present invention relates to embodiments of a method and apparatus for replacing a previously implanted prosthetic valve, such as a surgically implanted prosthetic heart valve, without removing the previously implanted valve from the body.

BACKGROUND

Prosthetic valves, such as prosthetic heart valves, are implanted in the body to replace a failing or diseased natural valve. Should the prosthetic valve begin to fail, it also may need to be replaced with another prosthetic valve. Surgically implanted, prosthetic heart valves, such as a prosthetic aortic valve, typically are replaced about every 15 years. The current method for replacing a surgically implanted, prosthetic heart valve involves open heart surgery wherein the patient's chest is opened and the existing prosthetic valve is removed and replaced with a new prosthetic valve. As can be appreciated, this is a traumatic and high risk procedure accompanied by substantial morbidity and mortality, and in some cases, cannot even be attempted due to the advanced age and/or medical condition of the patient.

Therefore, it would be preferable to replace a prosthetic heart valve with a percutaneously implanted valve that is delivered to the implantation site via the patient's vasculature and deployed within the previously implanted valve. However, because existing prosthetic heart valves can vary widely in size and shape, there are substantial difficulties associated with the development and validation of a percutaneously delivered replacement valve that is compatible with different types of existing prosthetic heart valves. More particularly, difficulties arise because a replacement valve that does not conform to the geometry of the previously implanted valve may not be able to adequately anchor to the previously implanted valve and/or form an effective seal with the previously implanted valve.

SUMMARY

In one aspect, the present disclosure concerns a percutaneously delivered adapter stent that is deployed within a previously implanted prosthetic valve and serves as an anchor or platform for implanting a percutaneously delivered replacement valve within the previously implanted valve. The replacement valve can be any known percutaneous valve. The adapter stent can be adapted to provide a suitable mounting platform for implanting a percutaneous replacement valve in a wide range of existing surgical valves, which typically vary widely in size and shape from patient to patient. In one advantageous feature, the adapter stent increases the frictional forces between the percutaneous replacement valve and the failing surgical valve, thereby providing a more predictable orientation and securement of the percutaneous replacement valve. Hence, this technique is particularly suited for replacing a surgically implanted prosthetic heart valve, but also could be used for replacing a percutaneously implanted prosthetic valve.

The adapter stent can be delivered to the implantation site via the patient's vasculature and positioned within the previously implanted valve. The stent can then be deployed to cause the stent to expand and become anchored to the inner surface of the previously implanted valve. Subsequently, the replacement valve can be positioned within the adapter stent and deployed to cause the replacement valve to expand and become anchored to the adapter stent.

In particular embodiments, the adapter stent and the replacement valve can be mounted on the same delivery catheter for delivery to the implantation site. In one implementation, for example, the adapter stent and the replacement valve can be crimped around respective first and second balloons of a double-balloon catheter. In this approach, the adapter stent is positioned in the previously implanted valve and expanded into contact with the previously implanted valve by inflating the first balloon. The catheter is then re-positioned to place the replacement valve in the deployed adapter stent, after which the valve is expanded into contact with the adapter stent by inflating the second balloon. In another implementation, the adapter stent and the replacement valve are self-expandable. The self-expandable adapter stent and valve can be mounted on a common delivery catheter adapted to retain the stent and the valve in compressed positions while they are advanced through the patient's vasculature. Using the catheter, the adapter stent and the valve can be successively positioned and deployed within the previously implanted valve.

The adapter stent in exemplary embodiments can comprise an expandable frame that mounts a flexible annular sealing member. The sealing member provides a seal between the previously implanted valve and the replacement valve to prevent or at least minimize blood flow between the original and replacement valves.

The adapter stent may be configured to have a length that is greater than the length of the previously implanted valve that needs to be replaced. This allows the stent to extend over the entire inner surface of the previously implanted valve to provide sufficient surface area for anchoring the replacement valve and to ensure that the previously implanted valve does not interfere with the positioning and deployment of the replacement valve. In certain embodiments, the adapter stent, when expanded, has enlarged end portions that flare or extend radially outwardly past the adjacent ends of the previously implanted valve to assist in securing the adapter stent in place.

In one representative embodiment, a method is provided for percutaneously implanting a replacement prosthetic valve at a site occupied by a previously implanted prosthetic valve. The method includes positioning an adapter stent within the previously implanted valve, deploying the adapter stent to cause the adapter stent to become anchored to the previously implanted valve, positioning the replacement valve within the deployed adapter stent, and deploying the replacement valve to cause the replacement valve to become anchored to the adapter stent.

In another representative embodiment, a method of percutaneously implanting a replacement prosthetic valve in a patient at a site occupied by a previously implanted prosthetic valve includes advancing a catheter carrying an adapter stent through the patient's vasculature to position the adapter stent within the previously implanted valve. The catheter also carries the replacement valve. The method further includes deploying the adapter stent to cause the adapter stent to become anchored to the previously implanted valve, re-positioning the catheter to position the replacement valve within the deployed adapter stent, and deploying the replacement valve to cause the replacement valve to become anchored to the adapter stent.

In another representative embodiment, an assembly is provided for percutaneous replacement of a previously implanted prosthetic valve without removal of the previously implanted valve. The assembly comprises an adapter stent comprising a frame and an annular sealing member. The adapter stent is adapted to be deployed within the previously implanted valve. The assembly also includes a percutaneous, replacement prosthetic valve comprising a frame and a flexible valve member. The valve is adapted to be deployed within the deployed adapter stent such that the sealing member provides a seal between the previously implanted valve and the replacement valve.

In yet another representative embodiment, an assembly for percutaneous replacement of a previously implanted prosthetic valve comprises a percutaneous, replacement prosthetic valve comprising a frame and a flexible valve member. The assembly also includes means for anchoring and sealing the replacement valve to the previously implanted valve, said means being separately deployable within the previously implanted valve prior to deploying the replacement valve within said means.

The foregoing and other features and advantages of the invention will become more apparent from the following detailed description, which proceeds with reference to the accompanying figures.

DETAILED DESCRIPTION

As used herein, the singular forms "a," "an," and "the" refer to one or more than one, unless the context clearly dictates otherwise.

As used herein, the term "includes" means "comprises." For example, a device that includes or comprises A and B contains A and B but may optionally contain C or other components other than A and B. A device that includes or comprises A or B may contain A or B or A and B, and optionally one or more other components such as C.

In one aspect, the present disclosure concerns a percutaneously delivered adapter stent that is deployed within a previously implanted prosthetic valve and serves as an anchor or platform for implanting a percutaneously delivered replacement valve within the previously implanted valve. As used herein, the term "stent" refers generally to any luminal structure. The replacement valve can be any known percutaneous valve. The adapter stent can be advanced through the patient's vasculature and positioned within the previously implanted valve. The adapter stent can then be deployed to cause the adapter stent to expand and become anchored to the inner surface of the previously implanted valve. The replacement valve can then be positioned within the adapter stent and deployed to cause the replacement valve to expand and become anchored to the adapter stent. In one respect, the adapter stent is configured to increase the frictional forces between the replacement valve and the failing previously implanted valve, thereby providing a more predictable orientation and securement of the replacement valve. In the following description, the adapter stent and the replacement valve are shown and described in connection with replacing a previously implanted aortic valve. However, the embodiments described herein can also be used to replace prosthetic valves implanted at other locations in the heart or in other body channels having native valves, such as veins or other organs.

Figure 1:
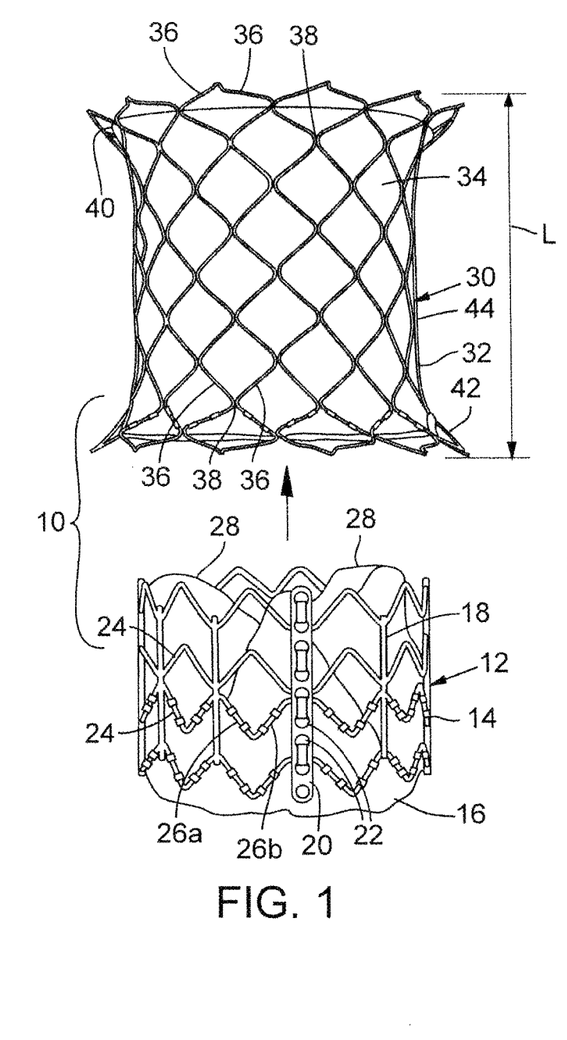
FIG. 1 is a side elevation view of one embodiment of an assembly comprising a percutaneous prosthetic valve and an adapter stent for anchoring the prosthetic valve within a previously implanted prosthetic valve.

FIG. 1 shows an assembly 10 comprising a percutaneous prosthetic heart valve 12 and an adapter stent 30, according to one embodiment. The adapter stent 30 can be deployed within a failing, previously implanted valve, such as the prosthetic aortic valve 60 shown in FIG. 4A. Once the adapter stent 30 is deployed within the previously implanted valve, the new valve 12 can be deployed within the adapter stent 30 to replace the previously implanted valve 60. The previously implanted valve 60 shown in the figures is a surgical valve (i.e., a valve implanted via open heart surgery), although the adapter stent 30 and the replacement valve 12 can also be deployed within a previously implanted percutaneous valve.

The valve 12 and the adapter stent 30 are each crimpable or compressible to a reduced diameter for percutaneous delivery to the implantation site, such as using a delivery catheter. When expanded to their functional size (FIG. 1), the outer diameter of the valve 12 desirably is approximately equal to the inner diameter of the adapter stent and the outer surface of the valve 12 generally conforms to an inner surface portion of the adapter stent 30 to promote attachment of the valve 12 to the adapter stent 30. Methods for implanting the adapter stent 30 and the valve 12 are described in greater detail below.

Figure 2:
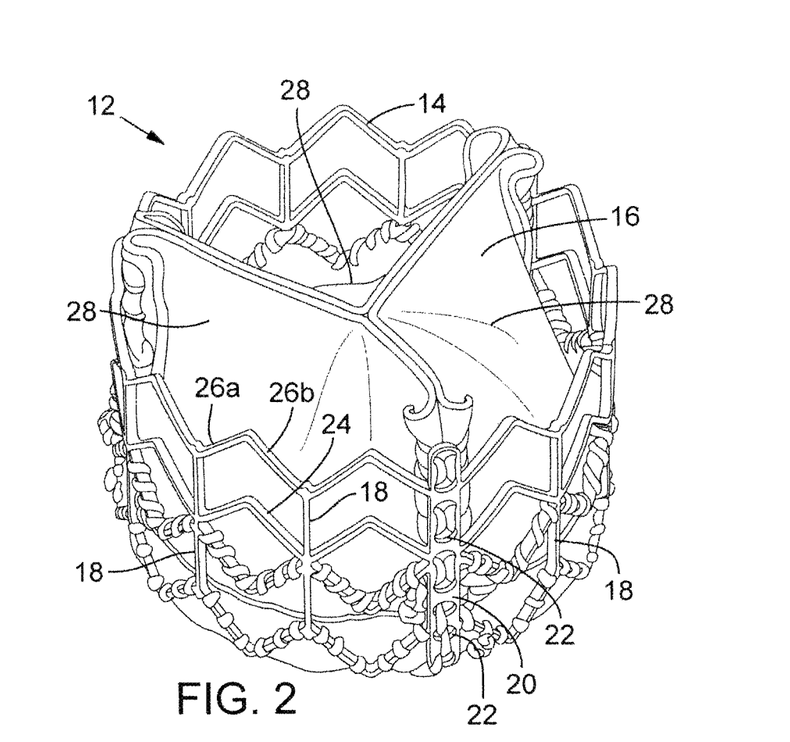
FIG. 2 is a perspective view of the prosthetic valve shown in FIG. 1.

As shown in FIGS. 1 and 2, the valve 12 in the illustrated embodiment includes an annular frame 14 that mounts a flexible valve member 16. The frame 14 in the illustrated embodiment comprises a plurality of angularly-spaced axial struts, or support members, 18 that extend axially (longitudinally) along the frame and a plurality of support posts, or beams, 20 (one of which is shown in FIGS. 1 and 2) spaced in the illustrated example at 120-degree intervals from each other around the frame 14. The support posts 20 can be formed with apertures 22 to facilitate attachment of the valve member 16 to the posts 20, such as, for example, by suturing the valve member 16 to the posts. The frame 14 can also include a plurality of axially-spaced, circumferential bands, or struts, 24 attached to the axial struts 18 and the support posts 20. The struts 24 are formed with multiple bends that allow the frame 14 to be crimped to a smaller diameter for delivery to an implantation site and expanded to its functional size for anchoring the valve assembly to the adapter stent 30 at the implantation site. For example, each of the struts 24 in the illustrated configuration includes a plurality of linear strut members 26a, 26b arranged in a zig-zag or saw-tooth configuration defining bends between adjacent strut members.

In alternative embodiments, the frame can have other configurations. For example, one or more of the circumferential bands 24 can have a curved or serpentine shape rather than a zig-zag shape. Further, the frame 14 can include various attachment elements (not shown), such as barbs, staples, flanges, and the like for enhancing the ability of the frame to anchor to the adapter stent 30.

The frame 14 can be made from any of various suitable ductile and/or elastic materials and is typically made of a metal, such as stainless steel, titanium, or other biocompatible metals. The frame 14 or components thereof can also be made from a shape memory alloy such as nickel titanium (NiTi) shape memory alloys, as marketed, for example, under the trade name Nitinol. The shape-memory components allow the valve 12 to be self-expandable; that is, the valve 12, when restrained in a radially compressed state by an outer restraint (e.g., a sheath covering the valve), automatically expands to its functional size when the outer restraint is removed.

The valve member 16 can have a leafed-valve configuration, such as the tricuspid valve configuration shown in the illustrated embodiment. The valve member 16 can be formed from three pieces of pliant material connected to each other at seams aligned with posts 20 to form collapsible leaflets 28 (FIG. 2). The valve member 16 can be made from biological matter, such as natural tissue, pericardial tissue (such as bovine, porcine or equine pericardium), a harvested natural valve or other biological tissue. Alternatively, the valve member 16 can be made from biocompatible polymers or similar materials.

Various other prosthetic valve configurations also can be used. Examples of other valves that can be utilized are disclosed in U.S. Pat. No. 6,730,118, U.S. Pat. No. 6,767,362, and U.S. Pat. No. 6,908,481, which are incorporated herein by reference.

The adapter stent 30 in exemplary embodiments includes an expandable frame 32 that mounts a flexible annular sealing member 34. The frame 32 is shown in FIG. 1 in its expanded, functional size, and is configured to be crimpable to a reduced diameter for percutaneous delivery, such as on a delivery catheter. The frame 32 can be made from any of various suitable ductile and/or elastic materials and is typically made of a metal, such as stainless steel, titanium, or other biocompatible metals. The frame 32 or components thereof can be made from a shape memory material, which allows the stent 30 to be self-expandable.

The frame 32 is the illustrated embodiment comprises a plurality of longitudinally extending, zig-zag struts 36 joined to each other at junctures 38. The frame 32 has a length L measured between the opposite ends thereof that desirably is greater than the length of the previously implanted valve that needs to be replaced. In this manner, the frame 32, when deployed within the previously implanted valve, can extend over the entire inner surface area of the previously implanted valve to provide sufficient surface area for anchoring the replacement valve 12 and to ensure that the previously implanted valve does not interfere with the positioning and deployment of the replacement valve 12. In particular embodiments, for example, the length L of the frame is about 10 mm to about 40 mm, with about 30 mm being a specific example.

As shown, the frame 32 in exemplary embodiments has a generally cylindrical intermediate portion 44 extending between the opposite end portions 40, 42, which are enlarged or flared relative to the intermediate portion 44 when the frame is expanded. Each end portion 40, 42 desirably expands to a diameter that is greater than the diameter of the previously implanted valve. Hence, when the adapter stent 30 is deployed within the previously implanted valve, the end portions 40, 42 can extend radially outwardly past the adjacent ends of the previously implanted valve to assist in securing the adapter stent in place.

Figure 4A:
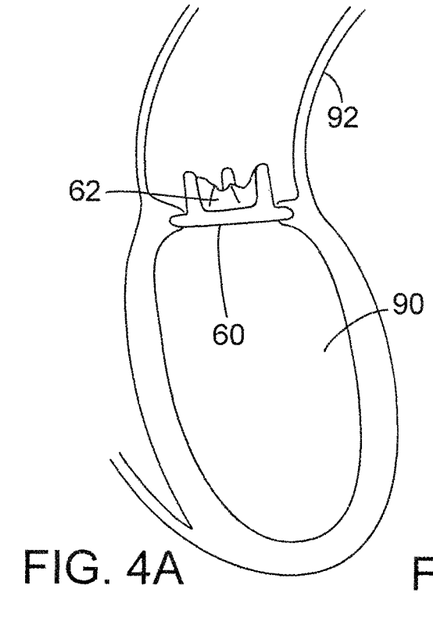
FIGS. 4A-4G illustrate the successive steps of one specific embodiment of an implantation procedure employing the double-balloon catheter shown in FIG. 2 for implanting the adapter stent and the prosthetic valve inside a failing surgically implanted, prosthetic valve previously implanted in the aortic orifice of a patient.

In alternative embodiments, the frame 32 can have various other shapes or configurations. For example, the frame 32 can be generally cylindrical or tubular along its entire length without enlarged end portions. The frame 32 optionally can be provided with various attachment elements (not shown), such as barbs, staples, flanges, and the like for enhancing the ability of the frame to anchor to the previously implanted valve 60 (FIG. 4A). If desired, the frame 32 may be provided with attachment elements along the inner surface for enhancing the ability of the frame 32 to securely engage the frame 14 of the percutaneously delivered replacement valve 12.

Figures 5, 6:
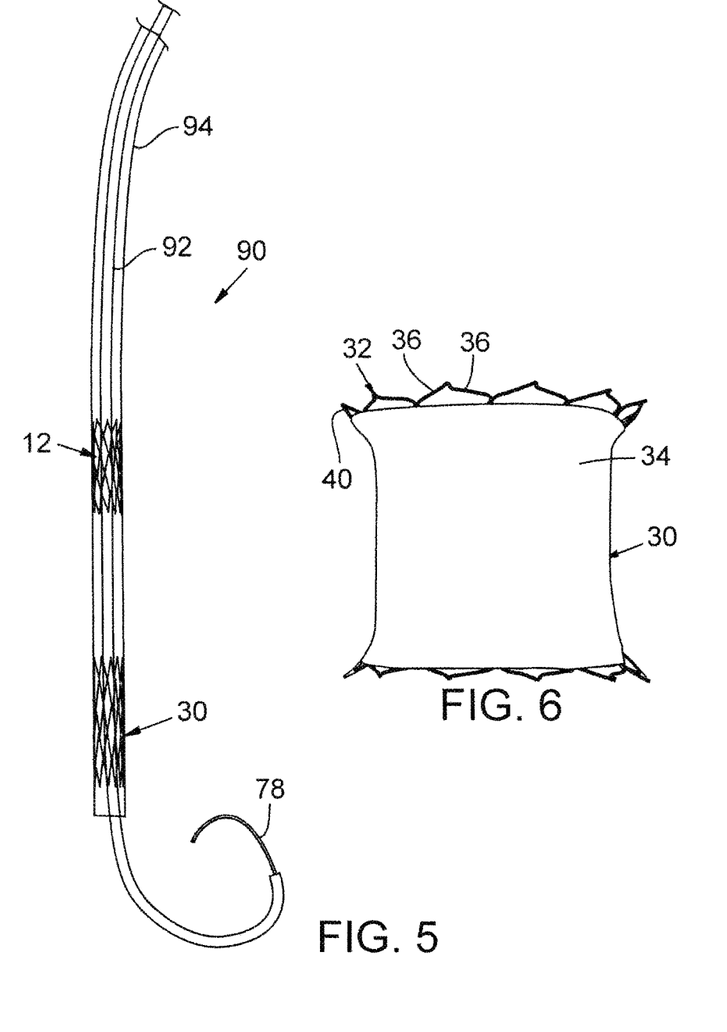
FIG. 5 is a schematic side view of one embodiment of delivery catheter that can be used to implant a self-expanding adapter stent and replacement valve inside a previously implanted valve.
FIG. 6 is a side elevation view of another embodiment of an adapter stent that can be used to anchor a replacement valve within a previously implanted prosthetic valve.

The sealing member 34 provides a seal between the previously implanted valve 60 and the replacement valve 12 to prevent or at least minimize blood flow between the valves. As shown in FIG. 1, the sealing member 34 desirably extends nearly the entire length of the frame 32 to maximize the surface area that can contact the previously implanted valve 60 and the replacement valve 12. In other embodiments, however, the sealing member can extend along only a portion of the frame 32, such as the intermediate portion 44. With reference to the embodiment shown in FIG. 1, the sealing member 34 is secured to the inner surface of the frame 32. Alternatively, the sealing member can be secured to the outer surface of the frame 32 as shown in FIG. 6 to prevent the leakage of blood. In another implementation, a sealing member 34 can be secured to both the inner and outer surfaces of the frame 32.

In particular embodiments, the sealing member 34 is made of a natural or synthetic biocompatible elastomeric material, such as foam rubber, thermoplastic elastomers (e.g., polyurethanes) or other polymeric elastomers, such as a polymeric sponge. The sealing member 34 can be secured to or formed on the frame using any suitable techniques or mechanisms, such as by suturing the sealing member to the frame or co-molding the sealing member to the frame. The sealing member 34 also can be formed on the frame using conventional coating techniques, such as spray coating, dip coating, or roll coating.

Figure 3:
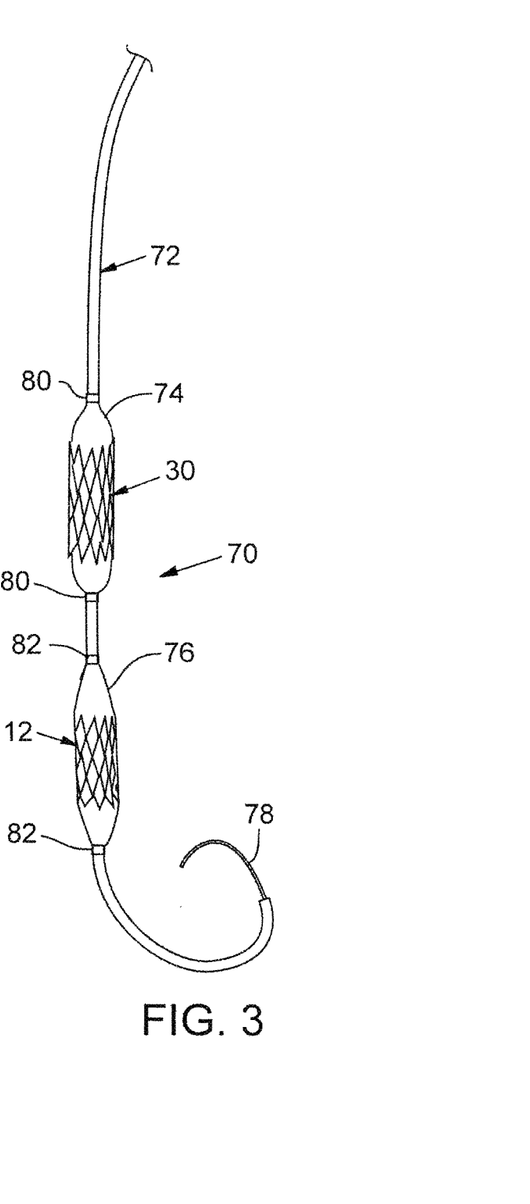
FIG. 3 is a schematic side view of an embodiment of a double-balloon catheter showing the prosthetic valve and the adapter stent of FIG. 1 crimped around respective balloons on the catheter for percutaneous delivery to an implantation site.

The valve 12 and the adapter stent 30 can be implanted using a double-balloon catheter. FIG. 3, for example, shows the distal end portion of an exemplary embodiment of a double-balloon catheter, indicated at 70. The catheter 70 includes a shaft 72, on which there are mounted first and second, spaced-apart balloons 74, 76, respectively, between a respective pair of rings 80, 82. The adapter stent 30 and the replacement valve 12 are crimped around the first balloon 74 and the second balloon 76, respectively. The shaft 72 contains two lumens (not shown), each of which is fluidly connected to a respective balloon 74, 76 for successive and separate inflation of each balloon. The shaft 72 also contains another lumen to accept a guide wire 78 so that the catheter can be advanced over the guide wire 78 for guiding the catheter through the patient's vasculature.

Figure 9:
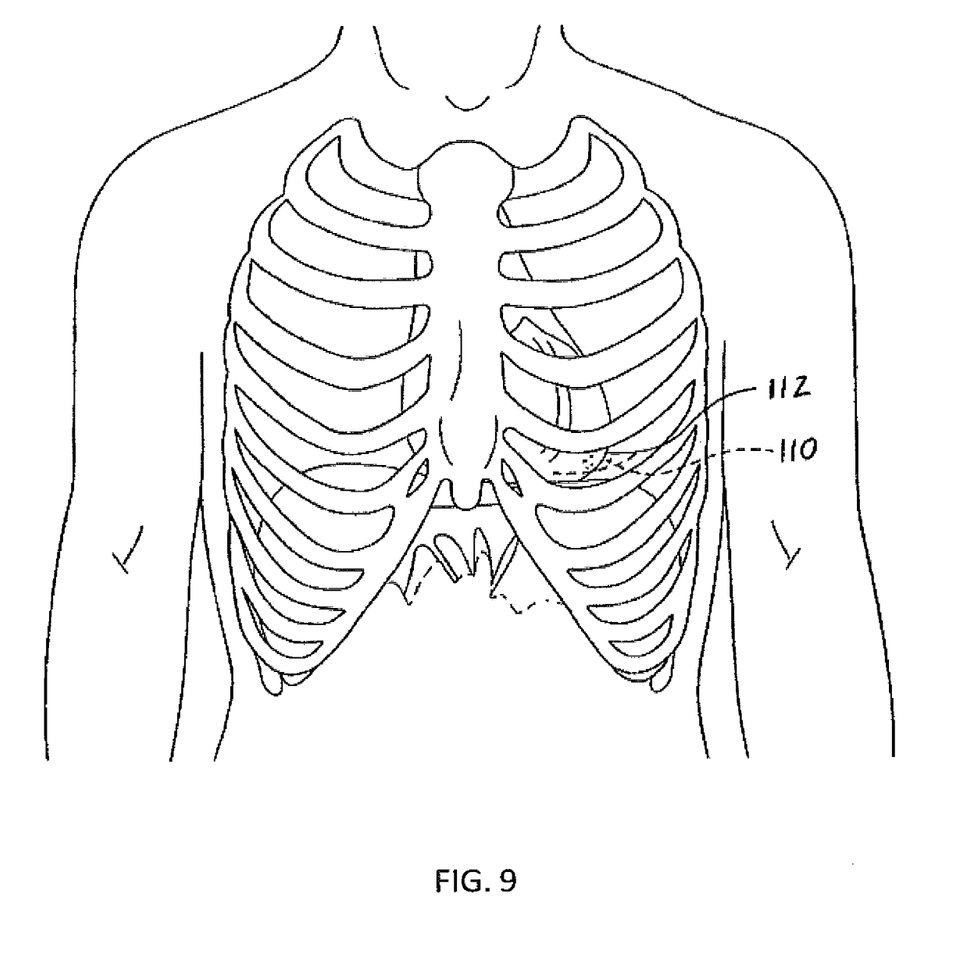
FIG. 9 shows a location in a patient's thorax where a catheter can be inserted for delivery through the left ventricle the heart.
Figure 10:
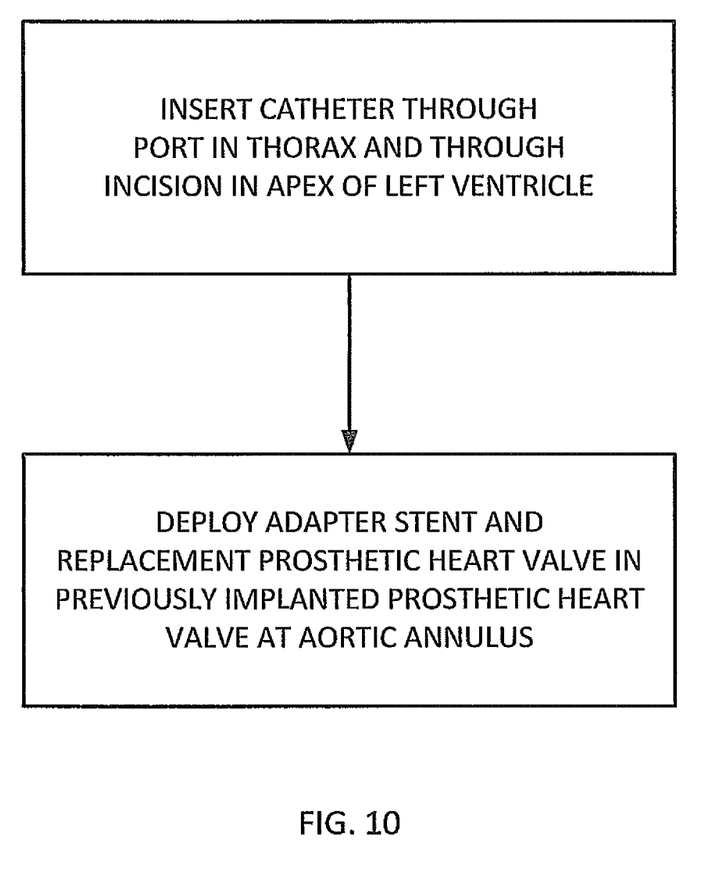
FIG. 10 is a flow chart illustrating an exemplary method disclosed herein.

The catheter 70 can be introduced percutaneously into the patient's vasculature (e.g., into a peripheral artery such as the femoral artery) and advanced to the implantation site. For example, for replacing a prosthetic aortic valve, the catheter in certain embodiments has a length of at least about 80 cm, usually about 90-100 cm, to allow transluminal positioning of the shaft from the femoral and iliac arteries to the ascending aorta. Alternatively, the shaft may have a shorter length, e.g. about 20-60 cm, for introduction through the iliac artery, through the brachial artery, through the carotid or subclavian arteries, or through a penetration in the aorta itself. In the femoral approach, the catheter desirably is long enough and flexible enough to traverse the path through the femoral artery, iliac artery, descending aorta and aortic arch. At the same time, the catheter desirably has sufficient pushability to be advanced to the ascending aorta by pushing on the proximal end, and has sufficient axial, bending, and torsional stiffness to allow the physician to control the position of the distal end, even when the catheter is in a tortuous vascular structure. Alternatively, as shown in FIGS. 9 and 10, the catheter may be passed through a port 110 between ribs in the patient's thorax above the heart and through an incision in the heart wall (e.g., through the apex of the left ventricle 112) or through an incision in the aortic arch, in a so-called minimally-invasive procedure.

Figure 4B:
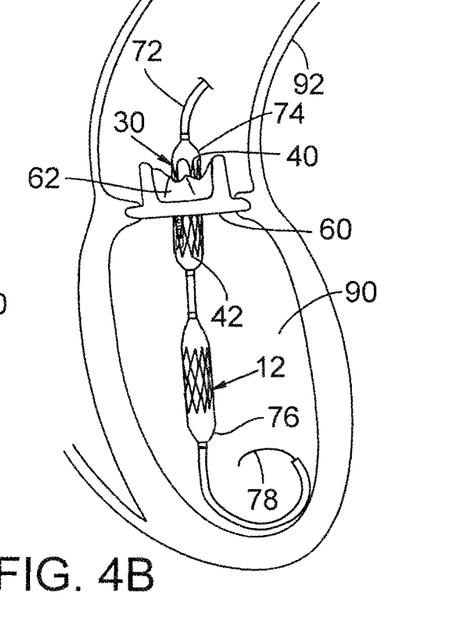

A procedure for implanting the valve 12 and the adapter stent 30 using the catheter 70, according one embodiment, is illustrated in FIGS. 4A-4G. FIG. 4A illustrates the previously implanted valve 60 implanted in the aortic annulus between the left ventricle chamber 86 and the ascending aorta 88. As noted above, the illustrated valve 60 is a surgical valve, although the adapter stent 30 and the replacement valve 12 can also be implanted within an existing percutaneous valve. The catheter 70 can be introduced percutaneously into the patient's vasculature and advanced to the implantation site using known techniques. For example, a blood vessel (e.g., the femoral artery) typically is dilated using a conventional dilator to allow an introducer sheath to be inserted into the blood vessel. The guide wire 78 can then be inserted into the blood vessel via the introducer sheath and advanced to the implantation site. Subsequently, the catheter 70 can be advanced over the guide wire 78 to position the adapter stent 30 in the previously implanted valve 60. More precisely, the adapter stent 30 desirably is positioned such that the end portions 40, 42 are located outside the adjacent ends of the previously implanted valve 60, as shown in FIG. 4B.

Figure 4C:
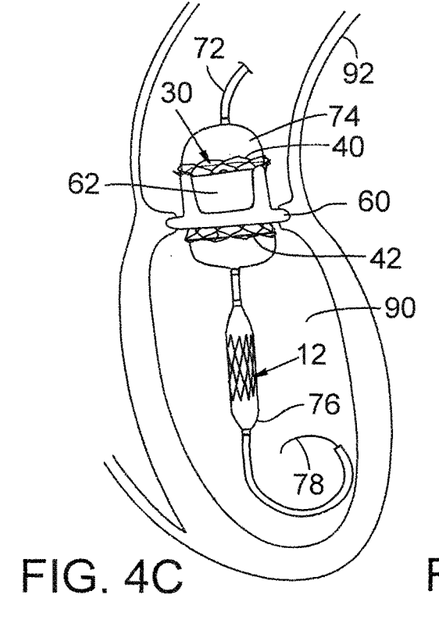
Figure 4D:
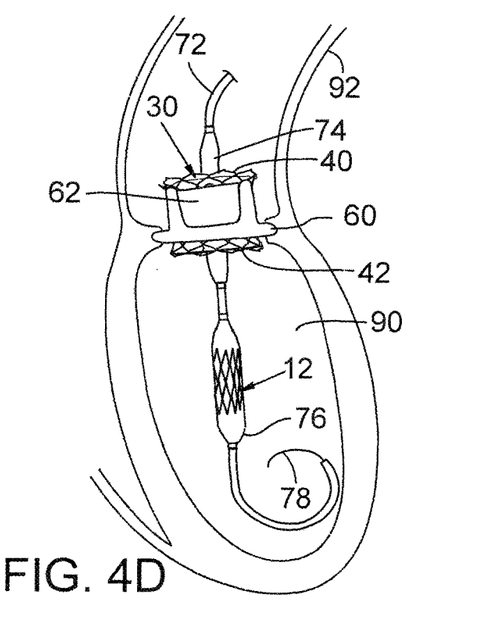

As depicted in FIG. 4C, the balloon 74 is then inflated to deploy the adapter stent 30, which expands to its functional size and engages the inner surface of the previously implanted valve 60. As shown, in its expanded stated, the end portion 40, 42 flare radially outwardly past the adjacent ends of the previously implanted valve to assist in retaining the adapter stent 30 in place against the valve 60. In addition, the adapter stent 30, in the illustrated example, also extends over the entire inner surface area of the existing valve 60 and causes the flexible leaflets 62 of the valve to expand radially outwardly, thereby providing a surface area suitable for mounting the replacement valve 12.

Figures 4E, 4F, 4G:
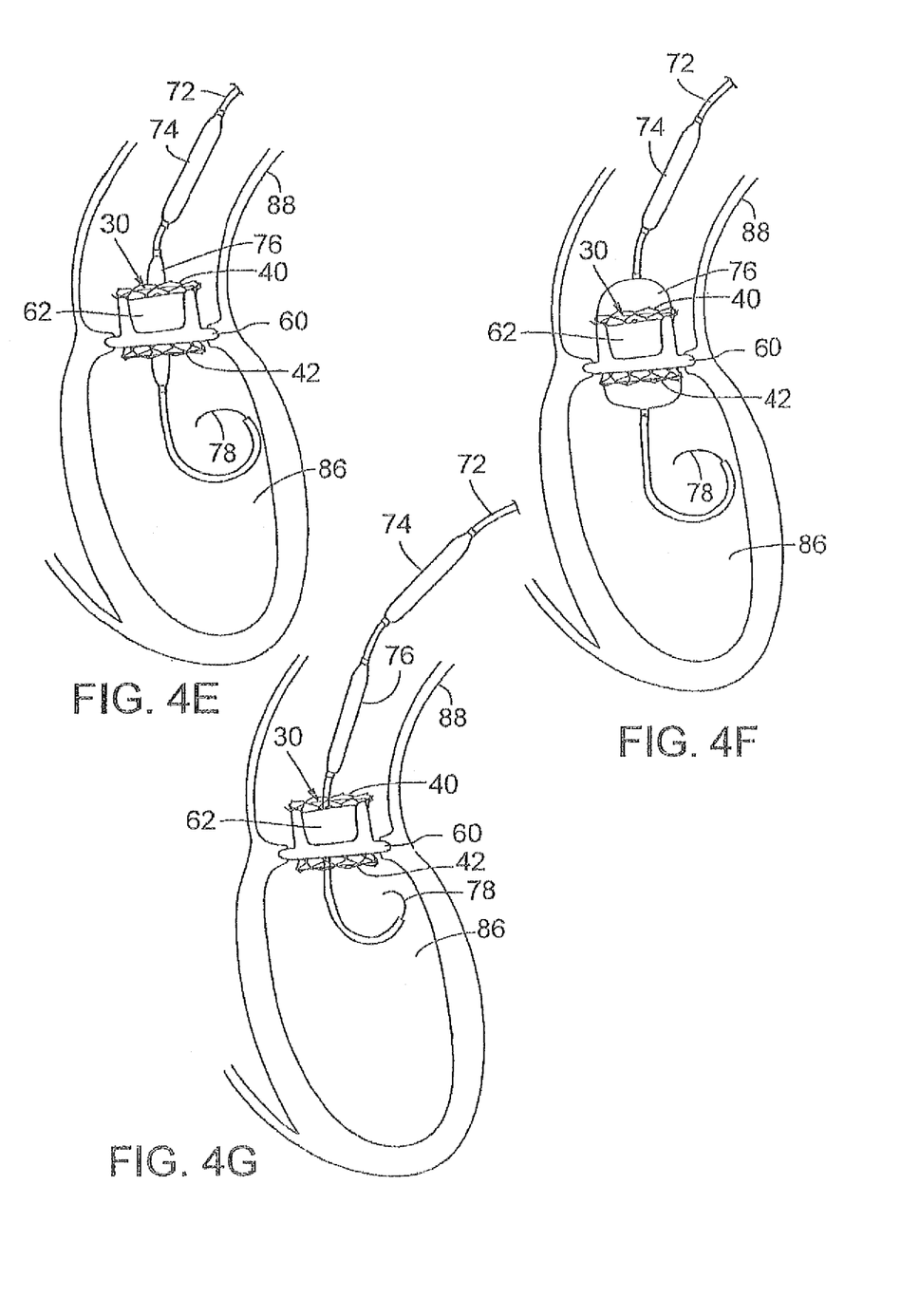

Thereafter, the balloon 74 is deflated (FIG. 4D) and the catheter 70 is retracted slightly to position the replacement valve 12 within the deployed adapter stent 30 (FIG. 4E). The second balloon 76 is then inflated to deploy the replacement valve 12, which expands to its functional size and engages the inner surface of the adapter stent 30 (FIG. 4F). Once the replacement valve 12 is deployed, the balloon 76 can be deflated and the catheter 70 can be removed from the body (FIG. 4G).

The adapter stent 30, as well as the valve 12, can be positioned at the implantation site with the assistance of fluoroscopy and radiopaque markers, ultrasonic imaging, and the like. For example, rings 80, 82 on the catheter shaft 72 can be made of any of various suitable metals that are visible during fluoroscopy for use in positioning the adapter stent and/or the valve. Alternatively, radiopaque markers can be provided on portions of the adapter stent 30 and/or the valve 12.

In an alternative approach, the replacement valve 12 can be mounted on the first balloon 74 and the adapter stent 30 can be mounted on the second balloon 76. In this approach, the adapter stent 30 is first deployed within the previously implanted valve 60 while the first balloon 74 and the replacement valve 12 are positioned in the aorta 88. After the adapter stent 30 is deployed, the catheter 70 is advanced further into the left ventricle 86 to position the first balloon 74 and the replacement valve 12 within the deployed adapter stent 30. The replacement valve 12 can then be deployed by inflating the first balloon 74.

As noted above, the frame 32 of the adapter stent 30 and the frame 14 of the replacement valve 12, or portions thereof, can be made of a shape-memory material, which allows the adapter stent 30 and the valve 12 to be self-expandable. FIG. 5 is a schematic view of the distal end portion of a delivery catheter, indicated at 90, which can be used to implant a self-expanding replacement valve and adapter stent in the previously implanted valve 60. The catheter 90 includes a shaft 92 and an outer sheath 94, which is moveable longitudinally relative to the shaft 92. The shaft 92 can include a lumen for receiving a guide wire 78. The valve 12 and the adapter stent 30 are mounted to the shaft 92 in their compressed states. The outer sheath 94 extends over the valve 12 and the adapter stent 30 to retain the valve and adapter stent in their compressed states until each is positioned for deployment at the implantation site.

The catheter 90 can be introduced into the body and advanced through the patient's vasculature in the same manner as the balloon catheter 70. The adapter stent 30 is first positioned in the previously implanted valve 60 and the outer sheath is retracted to expose the adapter stent 30, which permits the adapter stent to expand into contact with the previously implanted valve. The catheter 90 is then advanced slightly to position the valve 12 in the deployed adapter stent 30. The outer sheath 94 can then be retracted to expose the valve 12, which permits the valve to expand into contact with the adapter stent.

Although less desirable, the adapter stent 30 and the replacement valve 12 can be delivered and implanted at the site of the previously implanted valve using separate catheters. For example, the adapter stent 30 and the valve 12 can be mounted on separate balloon catheters. In this approach, the adapter stent 30 is implanted using a first balloon catheter, which is then removed from the body to allow a second balloon catheter carrying the replacement valve to be inserted into the body.

As noted above, surgical valves, such as valve 60, typically vary widely in size and shape from patient to patient. Advantageously, the adapter stent 30 can be adapted to provide a suitable mounting platform for implanting a percutaneous replacement valve in a wide range of surgical valves varying in size and shape.

Figure 7:
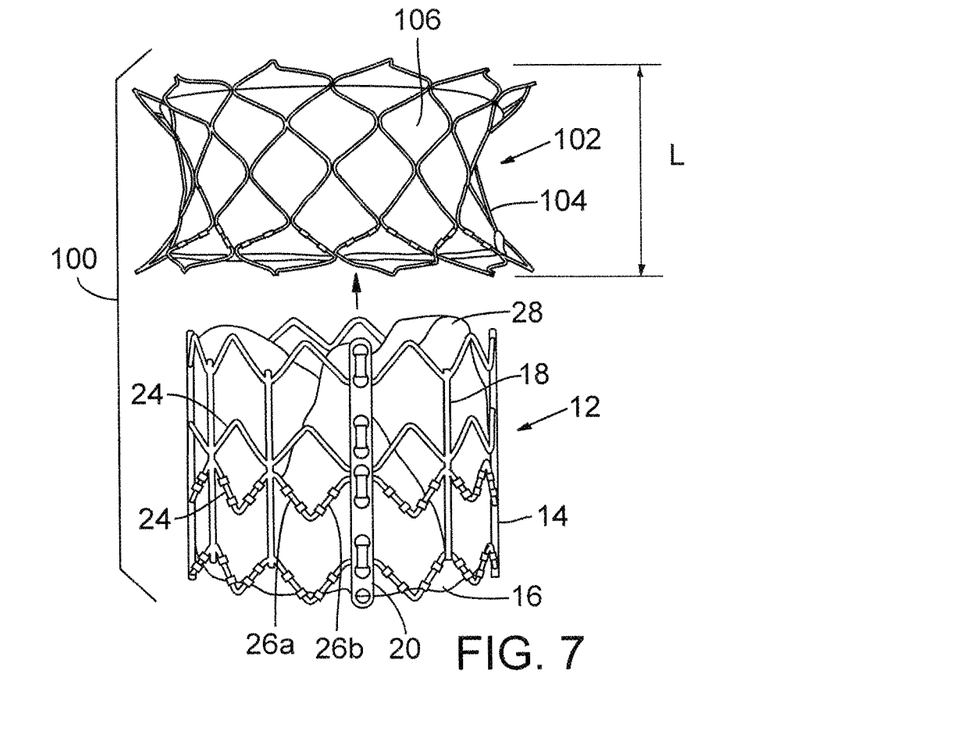
FIG. 7 illustrates another embodiment of an implantable assembly for replacing a previously implanted prosthetic valve.
Figure 8:
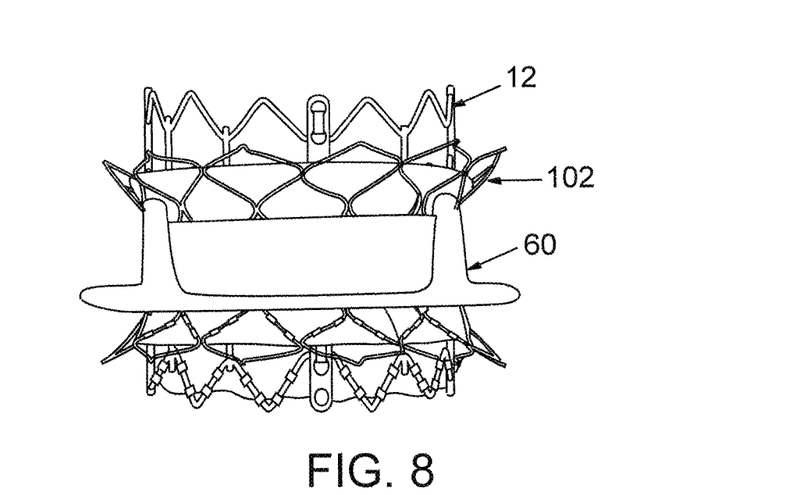
FIG. 8 illustrates the assembly of FIG. 7 deployed within a previously implanted surgical valve.

FIG. 7 illustrates another exemplary embodiment of an assembly 100 comprising a percutaneous prosthetic valve 12 and an adapter stent 102. The adapter stent 102, like adapter stent 30, includes a radially compressible and expandable frame 104 that mounts a flexible annular sealing member 106. FIG. 8 illustrates the adapter stent 102 and the prosthetic valve 12 deployed within a previously implanted surgical valve 60. The adapter stent 102 has a length L that is preferable greater than the length of the previously implanted valve 60 but need not be longer than the new valve 12. In certain embodiments, the adapter stent 102 has a length L of about 10 mm and the new valve 12 has a length of about 20 mm.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. I therefore claim as my invention all that comes within the scope and spirit of these claims.

I claim:

1. A method of implanting a replacement prosthetic heart valve within a defective previously implanted prosthetic heart valve that comprises leaflets configured to articulate between a functionally closed position and a functionally open position, the method comprising:

advancing an adapter stent and a replacement prosthetic heart valve through a port between ribs of a patient's thorax and through an apex of a left ventricle;

positioning the adapter stent within the defective previously implanted prosthetic heart valve, the previously implanted prosthetic heart valve having been implanted in an aortic annulus via open heart surgery, the adapter stent comprising an expandable tubular frame having an outer surface for contacting an interior region of the previously implanted prosthetic heart valve, the adapter stent further comprising a flexible annular sealing member disposed along an inner surface of the tubular frame;

radially expanding the adapter stent to cause the outer surface of the expandable tubular frame to become anchored within and to the interior region of the previously implanted prosthetic heart valve such that the adapter stent extends over an entire inner surface area of the previously implanted prosthetic heart valve;

after radially expanding the adapter stent within the previously implanted prosthetic heart valve, positioning the replacement prosthetic heart valve within the expanded adapter stent, the replacement prosthetic heart valve comprising a collapsible and expandable annular frame and a collapsible and expandable valve member mounted within the annular frame, the valve member comprising a tricuspid valve configuration formed with pericardial tissue and configured for allowing blood flow in only one direction when in an expanded condition; and radially expanding the replacement prosthetic heart valve within the adapter stent and the previously implanted prosthetic heart valve such that the replacement prosthetic heart valve extends beyond an inflow end of the adapter stent and extends beyond an outflow end of the adapter stent, and such that the adapter stent provides a stable platform for anchoring the replacement prosthetic heart valve by increasing frictional forces on the replacement prosthetic heart valve and the previously implanted prosthetic heart valve, and wherein, when the adapter stent and the replacement prosthetic heart valve are radially expanded within the previously implanted prosthetic heart valve, the flexible annular sealing member provides a seal between the previously implanted prosthetic heart valve and the replacement prosthetic heart valve, and wherein the flexible annular sealing member comprises an elastomeric material such that an outer surface of the replacement prosthetic heart valve conforms to an inner surface portion of the adapter stent.

2. The method of claim 1 wherein the adapter stent and the replacement prosthetic heart valve are mounted on a common delivery catheter, which is used to position the adapter stent and the replacement prosthetic heart valve at respective deployment positions.

3. The method of claim 2 wherein:
the adapter stent is mounted on a first balloon of the catheter and the replacement prosthetic heart valve is mounted on a second balloon of the catheter;
radially expanding the adapter stent comprises inflating the first balloon to cause the adapter stent to expand and engage the previously implanted prosthetic heart valve; and
radially expanding the replacement prosthetic heart valve comprises inflating the second balloon to cause the replacement prosthetic heart valve to engage the flexible annular sealing member.

4. The method of claim 2, wherein:
the adapter stent is self-expandable and is retained in a radially compressed state on the catheter by a sheath; and
radially expanding the adapter stent comprises withdrawing the sheath from the stent to allow the adapter stent to expand and engage the previously implanted prosthetic heart valve.

5. The method of claim 4, wherein:
the replacement prosthetic heart valve is self-expandable and is retained in a radially compressed state on the catheter by the sheath; and
radially expanding the replacement prosthetic heart valve comprises withdrawing the sheath from the replacement prosthetic heart valve to allow it to expand and engage the flexible annular sealing member.

6. The method of claim 1, wherein:
the adapter stent has a length that is greater than a length of the previously implanted prosthetic heart valve and wherein the adapter stent has a generally cylindrical intermediate portion and enlarged opposite end portions that are greater in diameter than the intermediate portion of the adapter stent when the adapter stent is radially expanded; and
when the adapter stent is radially expanded, the enlarged opposite end portions of the adapter stent are positioned outside of the previously implanted prosthetic heart valve to assist in retaining the adapter stent in place within the previously implanted prosthetic heart valve.

7. The method of claim 1, wherein the flexible annular sealing member comprises sponge rubber.

8. The method of claim 1, wherein the flexible annular sealing member extends along both the inner surface and an outer surface of the adapter stent.

9. The method of claim 1, wherein the tubular frame of the adapter stent has a length of at least about 10 mm.

10. The method of claim 1, wherein the replacement prosthetic heart valve has an outer diameter in an expanded condition which is approximately equal to an inner diameter of the adapter stent in an expanded condition.

11. The method of claim 1, wherein the tubular frame of the adapter stent further comprises attachment elements along an outer surface for enhancing the ability of the adapter stent to anchor to the previously implanted prosthetic heart valve.

12. A method of implanting a replacement prosthetic heart valve within a defective surgically implanted prosthetic heart valve, the method comprising:

advancing a catheter carrying an adapter stent through a port between a patient's ribs and through an apex of the left ventricle to position the adapter stent within the surgically implanted prosthetic heart valve, the surgically implanted prosthetic heart valve having been previously implanted in an aortic annulus via open heart surgery, the catheter also carrying the replacement prosthetic heart valve;

deploying the adapter stent to cause the adapter stent to become anchored to an interior region of the defective surgically implanted prosthetic heart valve, the adapter stent comprising a generally tubular frame having an inner surface and an outer surface and a compressible sealing member disposed along both the inner surface and the outer surface of the generally tubular frame, wherein the adapter stent comprises a substantially cylindrical portion that has a substantially constant diameter extending along the length of the adapter stent where the adapter stent overlies the interior region of the defective surgically implanted prosthetic heart valve;

re-positioning the catheter, after deploying the adapter stent, to position the replacement prosthetic heart valve within the deployed and expanded adapter stent; and deploying the replacement prosthetic heart valve to cause the replacement prosthetic heart valve to expand and contact the compressible sealing member on the inner surface of the adapter stent such that the replacement prosthetic heart valve extends beyond an inflow end of the adapter stent and extends beyond an outflow end of the adapter stent, wherein the compressible sealing member of the adapter stent comprises an elastomeric material such that an outer surface of the replacement prosthetic heart valve conforms to an inner surface portion of the adapter stent to form a seal between the surgically implanted prosthetic heart valve and the replacement prosthetic heart valve after expansion of the replacement prosthetic heart valve, and wherein the adapter stent provides a stable platform for anchoring the replacement prosthetic heart valve by increasing frictional forces on the replacement prosthetic heart valve and the surgically implanted prosthetic heart valve.

13. The method of claim 12 wherein:

the adapter stent is mounted on a first balloon of the catheter and the replacement prosthetic heart valve is mounted on a second balloon of the catheter;

deploying the adapter stent comprises inflating the first balloon to cause the adapter stent to expand and engage the surgically implanted prosthetic heart valve; and deploying the replacement prosthetic heart valve comprises inflating the second balloon to cause the replacement prosthetic heart valve to contact the compressible sealing member of the adapter stent.

14. The method of claim 12, wherein when the adapter stent is deployed, opposite end portions of the adapter stent extend outside opposite ends of the defective surgically implanted prosthetic heart valve and flare radially outwardly with respect to the opposite ends of the defective surgically implanted prosthetic heart valve.

15. A method of implanting a replacement prosthetic heart valve within a previously implanted prosthetic heart valve, the method comprising:

positioning an adapter stent within a previously implanted prosthetic heart valve, the previously implanted prosthetic heart valve having been implanted in an aortic annulus via open heart surgery, the adapter stent comprising an expandable tubular frame having an outer surface for contacting an interior region of the previously implanted prosthetic heart valve, the adapter stent further comprising a flexible annular sealing member comprising an elastomeric material and disposed on the expandable tubular frame;

radially expanding the adapter stent to cause the outer surface of the expandable tubular frame to become anchored to the interior region of the previously implanted prosthetic heart valve, such that the adapter stent extends over an entire inner surface area of the previously implanted prosthetic heart valve and an outflow end of the adapter stent flares radially outwardly past an outflow end of the previously implanted prosthetic heart valve and an inflow end of the adapter stent flares radially outwardly past an inflow end of the previously implanted prosthetic heart valve;

after radially expanding the adapter stent within the previously implanted prosthetic heart valve, positioning a replacement prosthetic heart valve within the expanded adapter stent; and radially expanding the replacement prosthetic heart valve to expand within the adapter stent and the previously implanted prosthetic heart valve such that the replacement prosthetic heart valve extends axially beyond the inflow end of the adapter stent and extends axially beyond the outflow end of the adapter stent, such that the adapter stent provides a stable platform for anchoring the replacement prosthetic heart valve;

wherein, when the adapter stent and the replacement prosthetic heart valve are radially expanded within the previously implanted prosthetic heart valve, the flexible annular sealing member allows an outer surface of the replacement prosthetic heart valve to conform to an inner surface portion of the adapter stent to provide a seal between the previously implanted prosthetic heart valve and the replacement prosthetic heart valve.

* * * * *